United States Patent [19]

Bürki

[11] Plant 4,817

[45] Jan. 26, 1982

[54] KALANCHOE PLANT

[75] Inventor: Moritz Bürki, Langendorf, Switzerland

[73] Assignee: Mikkelsens, Inc., Ashtabula, Ohio

[21] Appl. No.: 186,502

[22] Filed: Sep. 11, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A Kalanchoe plant named Regulus having bright orange flower color and floriferous habit, compact, and relatively slow growth habit, freely branching habit, excellent and full flower placement, adaptability to production in 10 to 15 cm. pots, and a flowering time of 11 weeks in summer and 15 weeks in winter.

1 Drawing Figure

The present invention relates to a new and distinctive variety of kalanchoe plant, botanically known as kalanchoe, and known by the cultivar name Regulus.

The new cultivar was developed by me through controlled breeding by crossing Feuerball (seed parent) with Annette (pollen parent). Feuerball is disclosed in U.S. Plant Pat. No. 3,861, granted Apr. 13, 1976 to Adolf Grob. Asexual reproduction by stem cuttings has shown that the unique features of this new kalanchoe are stabilized and are reproduced true to type in successive propagations.

The following characteristics distinguish the new kalanchoe from both its parent varieties and other cultivated kalanchoes of this type known and used in the floriculture industry:

1. Regulus was selected especially for its outstanding bright orange flower color, its compact growth habit, and its freely branching ability.
2. Growth is relatively slow, being comparable to that of Feuerball.
3. Freely branching, with shoots formed at every node, comparable to that of Feuerball.
4. Proper scheduling makes Regulus suitable for production in 10 to 15 cm. pots.
5. Total flower placement provides an attractive flower display, with flowers of the terminal and side peduncles at approximately the same height, resulting in a slightly domeshaped flower bouquet.
6. To reduce peduncle elongation after flower initiation, plants can be treated with B9.
7. Regulus is highly floriferous, with numerous flowers formed at every shoot.
8. Flowering time is approximately 11 weeks in summer to 15 weeks in winter after start of short days.

The accompanying colored photograph illustrates the overall appearance of this variety as a face view of the plant and showing the colors as true as it is reasonably possible to obtain in a colored reproduction of this type.

The following is a detailed description of my new kalanchoe variety based on plants produced under commercial practices in the greenhouses of Wyss Samen und Pflanzen A.G., Solothurn, Switzerland, and the greenhouses of Mikkelsens Inc., Ashtabula, Ohio. Color references are made to the Royal Horticultural Society Color Chart except where general terms of ordinary dictionary significance are used.

Parentage: A controlled cross of the cultivar Feuerball as the seed parent and the cultivar Annette as the pollen parent.

Propagation:

*Type cutting.*—Tip cutting, with stems up to 2 cm. long.

*Time to root.*—10 days at 21° C. summer, 14 days at 21° C. winter.

*Rooting habit.*—Fibrous, many very fine roots.

PLANT DESCRIPTION

Form: Upright, short, compact. Growing and scheduling practices can produce small plants in 10 cm. pots or large plants in 15 cm. pots.

Habit of growth: Relatively slow for this type of plant. Generally, shoots are formed at every node.

Foliage description: Leaves simple, opposite, generally symmetrical.

*Size.*—Average full grown leaf of a flowering plant in a 10 cm. pot is 100 mm. long and 65 mm. wide. Plants in larger pots have larger full grown leaves.

*Shape.*—Elliptic to ovate, apex acute to obtuse, base truncate to obtuse.

*Texture.*—Glabrous, coriaceous, succulent.

*Margin.*—Crenate.

*Color.*—Young foliage, top side Yellow-Green 147A, under side Yellow-Green 147B. Mature foliage, top side Yellow-Green 147A, under side Yellow-Green 147B. Under high light conditions mature foliage develops a red margin and apex.

FLOWERING DESCRIPTION

Flowering habits: Inflorescence of each shoot is formed by dichotomous branching, starting with opening of terminal flower of main axis followed by terminal flowers of the side branches of the inflorescence. Opening of new buds will continue for two months or more. Individual flowers last two weeks or more after opening.

Natural flowering season: Late January.

Flowering time: Under controlled daylength at 20° C. in summer, 11 weeks; in winter, 15 weeks. Flowering time depends on temperature, light intensity and other growing conditions.

Flower buds: Generally oblong, up to 16 mm. long, developing to tubular as flower petals mature, sheathed with four green sepals; corolla at maturity 13 mm. long.

Flowers borne: Compound dichasial cyme on strong peduncles. Peduncle length depends on growing conditions and B9 applications. Pedicels up to 5 mm. long.

Quantity of flowers: Very floriferous; main axis and main side shoots has 50 or more flowers with new buds continuing to develop.

Petals:

*Shape.*—Nearly round, apex cuspidate.

*Color.*—Top side when opening Orange-Red 32A, fading to Orange-Red 30A-B. Under side: One side Orange 29B; one side Orange-Red 32B.

*Number of petals.*—Four, united in corolla, salverform; petals 6 mm. in diameter, total flower diameter 15 mm.

Reproductive organs:

*Stamens.*—Eight in number. Anther shape: flat, elliptical, color yellow. Filament color: light green. Pollen color: yellow.

*Pistels.*—Stigma shape: flat, crystalline, color greenish white. Style color: light green. Ovaries: 4 celled, 7 mm. long, color green.

Disease resistance: No known kalanchoe diseases observed to date. Cultivar is highly resistant to mildew.

I claim:

1. A new and distinct cultivar of Kalanchoe plant known by the cultivar name Regulus, as described and illustrated, and particularly characterized by the combined characteristics of bright orange flower color and floriferous habit, compact and relatively slow growth habit, freely branching habit, excellent and full flower placement, adaptability to production in 10 to 15 cm. pots, and by its flowering time of 11 weeks in summer and 15 weeks in winter after start of short days.

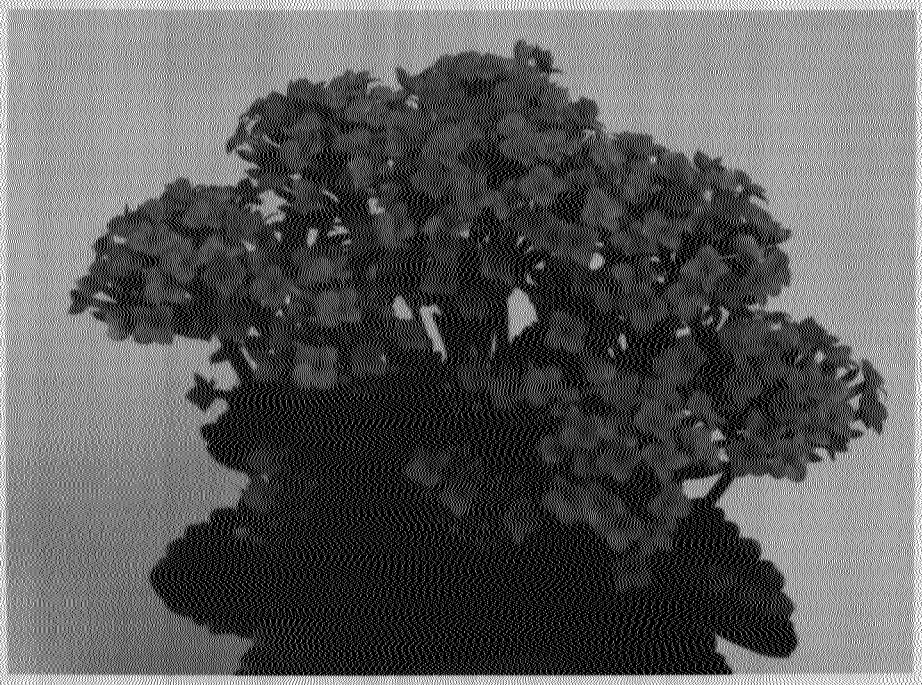

* * * * *